US008535289B1

(12) United States Patent
Forbes

(10) Patent No.: US 8,535,289 B1

(45) Date of Patent: Sep. 17, 2013

(54) VIAL ATTACHMENT PLIERS

(76) Inventor: Vincent C. Forbes, Chesapeake, VA (US)

( * ) Notice: Subject to any disclaimer, the term of this patent is extended or adjusted under 35 U.S.C. 154(b) by 0 days.

(21) Appl. No.: 13/558,115

(22) Filed: Jul. 25, 2012

(51) Int. Cl.
*A61B 19/00* (2006.01)

(52) U.S. Cl.
USPC .......... 604/408

(58) Field of Classification Search
USPC .......... 604/403–416; 81/318–324, 351–354, 81/407–414
See application file for complete search history.

(56) References Cited

U.S. PATENT DOCUMENTS

| | | | | |
|---|---|---|---|---|
| 717,033 | A | 12/1902 | Schneider | |
| 2,084,529 | A | 6/1937 | Landau | |
| 2,514,130 | A | 7/1950 | Jones | |
| 3,395,724 | A | 8/1968 | Hamel | |
| 4,893,530 | A | 1/1990 | Warhei | |
| 5,339,511 | A | 8/1994 | Bell | |
| 5,364,386 | A | 11/1994 | Fukuoka | |
| 5,438,892 | A | 8/1995 | Bell | |
| 5,529,097 | A * | 6/1996 | Campbell | 141/51 |
| 6,070,761 | A | 6/2000 | Bloom | |
| 6,422,273 | B1 | 7/2002 | Campbell | |
| 2004/0073189 | A1 | 4/2004 | Wyatt | |
| 2010/0218846 | A1 | 9/2010 | Kriheli | |
| 2011/0004145 | A1 | 1/2011 | Beiriger | |
| 2011/0034899 | A1 | 2/2011 | Thome | |
| 2011/0112501 | A1 | 5/2011 | Garfield | |

FOREIGN PATENT DOCUMENTS

| | | | |
|---|---|---|---|
| EP | 577569 | A1 | 1/1994 |

* cited by examiner

*Primary Examiner* — Philip R Wiest
(74) *Attorney, Agent, or Firm* — Wooten & Shaddock, PLC

(57) ABSTRACT

Vial attachment pliers that include a handle; a static arm that includes a recessed vial adapter slot and extends from the handle such that the longitudinal axis of the static arm is substantially perpendicular to the longitudinal axis of the handle; a guide rod that extends from the static arm such that the longitudinal axis of the guide rod is substantially perpendicular to the longitudinal axis of the static arm; a dynamic arm having a vial slot that is slidably attached to the guide rod; a lever pivotably attached to the handle; and a connector bar connecting the lever to the dynamic arm, such that as the lever pivots relative to the handle, the dynamic arm is urged to slide along the guide rod.

19 Claims, 6 Drawing Sheets

VIAL ATTACHMENT PLIERS

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING

Compact Disc Appendix

Not Applicable.

NOTICE OF COPYRIGHTED MATERIAL

The disclosure of this patent document contains material that is subject to copyright protection. The copyright owner has no objection to the reproduction by anyone of the patent document or the patent disclosure, as it appears in the Patent and Trademark Office patent file or records, but otherwise reserves all copyright rights whatsoever. Unless otherwise noted, all trademarks and service marks identified herein are owned by the applicant.

BACKGROUND OF THE INVENTION

1. Field of the Invention

This invention relates generally to the field of medical devices. More specifically, the present invention relates to vial attachment pliers to aid in the connection of a vial to an IV bag.

2. Description of Related Art

Intravenous (IV) therapy involves the introduction of liquids directly into a patient's vein. IV therapy is a relatively common procedure in many areas of clinical practice to deliver drugs or medications, to correct electrolyte imbalances, for blood transfusions, or for body fluid replacement. When compared to other routes of administration, the IV therapy is the fastest way to deliver fluids and medications throughout a patient's body.

Intravenous drugs for use in IV therapy come in a variety of presentations, one of the most common being rubber-capped vials.

Generally, to introduce a drug or medication into an IV bag from a rubber-capped vile, a plastic flip-top cap is removed from the vial to expose the central portions of the rubber stopper. The top of the vial, including the rubber stopper, is cleaned with an antiseptic solution and allowed to dry. An IV vial adapter is fitted to the IV bag and the vial is placed within the adapter so that the IV adapter spike is positioned above and proximate the center of the rubber stopper.

Then, while holding the adapter and the vial, the vial is manually pressed against the adapter spike until the spike penetrated the vial stopper.

BRIEF SUMMARY OF THE INVENTION

However, the typical method for attaching a vial to an IV vial adapter can prove to be rather difficult and, over time, can cause carpal tunnel syndrome. Nurses have complained that applying excessive force to insert the vial into the IV bag vial adapter has caused hand/wrist pain and/or discomfort and, in some cases, has cause carpal tunnel syndrome.

In various exemplary, non-limiting embodiments, the upper, static arm has a slit or opening that slides over the neck of the IV bag vial adapter. The neck of the vial bottle is secured in a substantial U-shape slot in the lower jaw. In certain exemplary embodiments, a rubber padding or other cushioning material is provided within the U-shape slot to protect the vial's neck from damage. The vial attachment pliers are designed to accommodate various size vials.

When the lever is pivoted, or squeezed, towards the handle, the lower, dynamic arm is forced, via a connector bar, to travel upward. The upward motion of the dynamic arm pushes the vial upward and inserts the vial into the IV bag vial adapter. This eliminates stress and/or strain on the hand/wrist.

In various exemplary embodiments, the vial attachment pliers comprise an elongate handle having a longitudinal axis, a static arm having a longitudinal axis, wherein the static are extends from the handle such that the longitudinal axis of the static arm is substantially perpendicular to the longitudinal axis of the handle, and wherein the static arm includes a vial adapter slot, a guide rod having a longitudinal axis, wherein the guide rod extends from the static arm such that the longitudinal axis of the guide rod is substantially perpendicular to the longitudinal axis of the static arm, a dynamic arm having a longitudinal axis, wherein the dynamic arm is slidably attached to the guide rod such that the dynamic arm is slidable along at least a portion of the guide rod, and wherein the longitudinal axis of the dynamic arm remains parallel to the longitudinal axis of the static arm as the dynamic arm slides along the guide rod, and wherein the dynamic arm includes a vial slot, a lever, wherein the lever is pivotably attached to the handle, a connector bar connecting the lever to the dynamic arm, such that as the lever pivots relative to the handle, the dynamic arm is urged to slide along the portion of the guide rod.

In various exemplary embodiments, the vial attachment pliers have a spring loaded handle.

Accordingly, this invention provides vial attachment pliers that allow a user to secure a vial bottle to an IV bag vial adapter without applying excessive force.

This invention separately provides vial attachment pliers that reduced the pain/discomfort to a user's hand and/or wrist when securing a vial to an IV bag vial adapter.

This invention separately provides vial attachment pliers that accommodate various size vials.

This invention separately provides vial attachment pliers that can be easily manipulated by a user.

These and other features and advantages of this invention are described in or are apparent from the following detailed description of the exemplary, non-limiting embodiments.

BRIEF DESCRIPTION OF THE SEVERAL VIEWS OF THE DRAWINGS

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a basis for the claims and as a representative basis for teaching one skilled in the art to employ the present invention.

The exemplary embodiments of this invention will be described in detail, with reference to the following figures, wherein like reference numerals refer to like parts throughout the several views, and wherein.

DETAILED DESCRIPTION OF THE INVENTION

Figure 1:
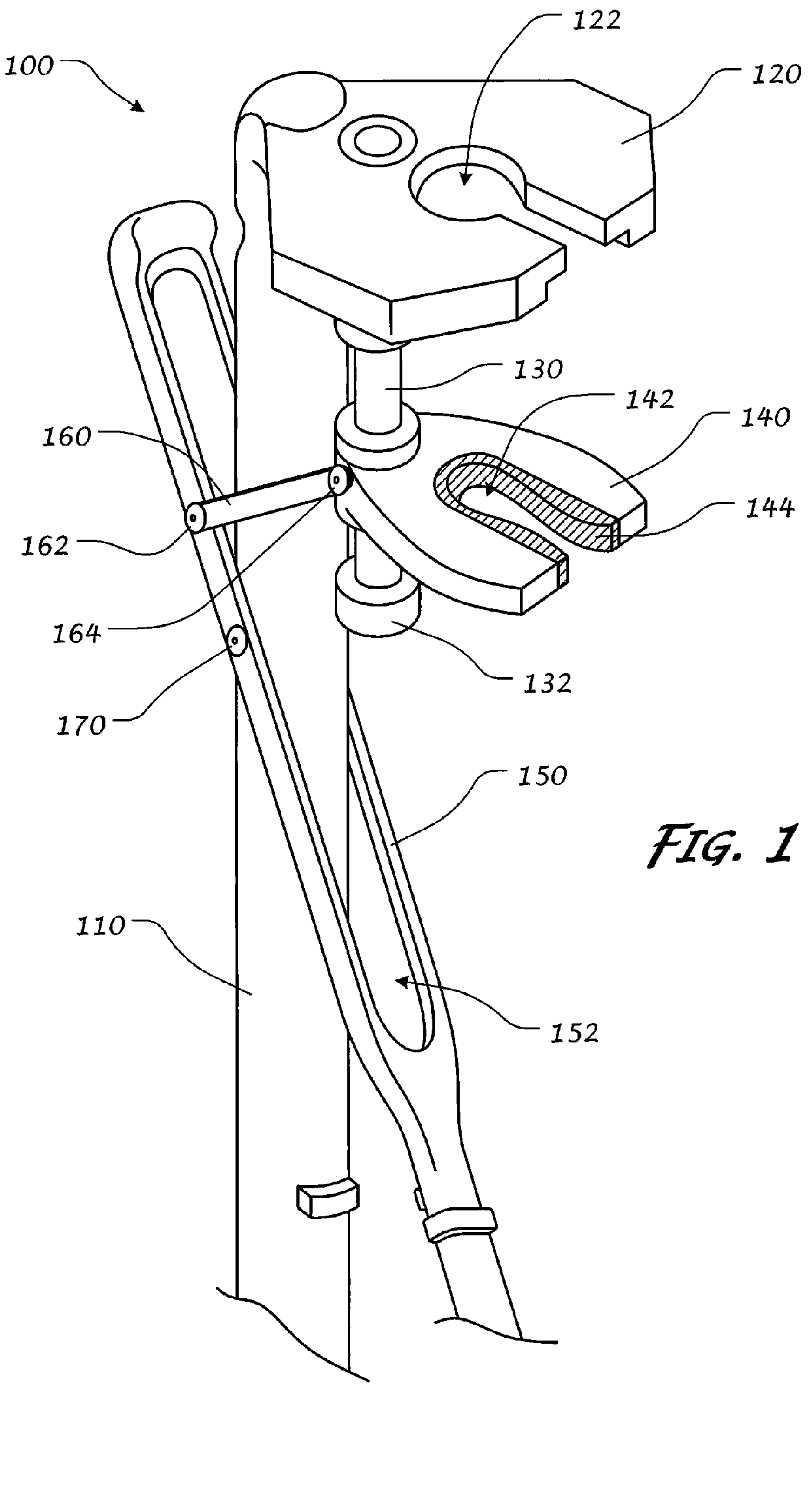
FIG. 1 shows a perspective view of a first exemplary embodiment of vial attachment pliers, according to this invention.
Figure 2:
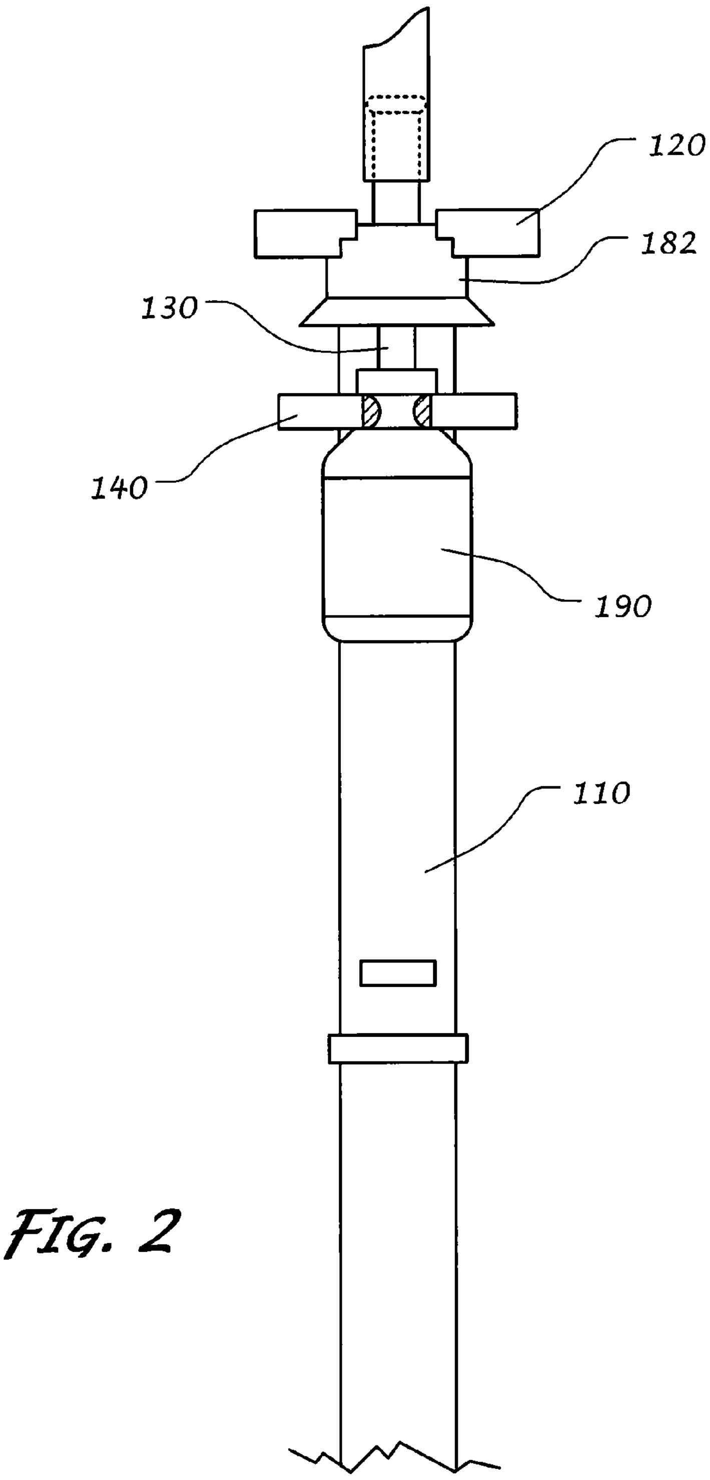
FIG. 2 shows a front view of certain elements of an exemplary embodiment of vial attachment pliers, according to this invention.
Figure 3:
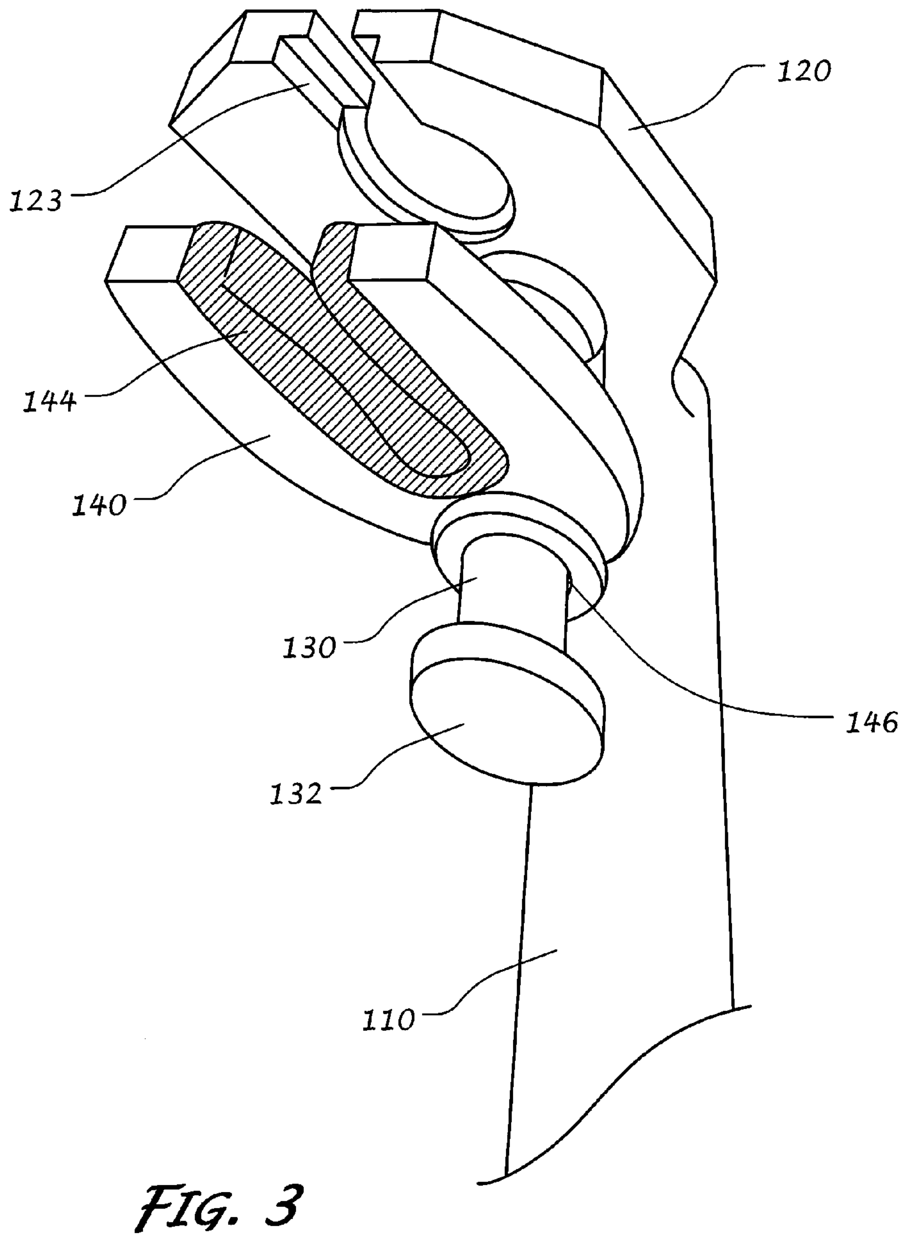
FIG. 3 shows a bottom perspective view of certain elements of an exemplary embodiment of vial attachment pliers, according to this invention.

For simplicity and clarification, the design factors and operating principles of the vial attachment pliers according to this invention are explained with reference to various exemplary embodiments of vial attachment pliers according to this invention. The basic explanation of the design factors and operating principles of the vial attachment pliers is applicable for the understanding, design, and operation of the vial attachment pliers of this invention. It should be appreciated that the vial attachment pliers can be adapted to many applications where a rubber-capped vile must be inserted into an IV bag vial adapter.

It should also be appreciated that the terms "vial", "vial bottle", "pliers", and "vial attachment pliers" are used for basic explanation and understanding of the operation of the systems, methods, and apparatuses of this invention. Therefore, the terms "vial", "vial bottle", "pliers", and "vial attachment pliers" are not to be construed as limiting the systems, methods, and apparatuses of this invention. Thus, the terms "vial" and "vial bottle" are to be understood to broadly include any structures or devices capable of containing a liquid or solution.

Turning now to the drawing Figs., FIGS. 1-7 show certain elements and/or aspects of a first exemplary embodiment of the vial attachment pliers 100, according to this invention. In illustrative, non-limiting embodiment(s) of this invention, as illustrated in FIGS. 1-7, the vial attachment pliers 100 comprise at least some of an handle 110, a static arm 120, a guide rod 130, a dynamic arm 140, a lever 150, and a connector bar 160.

In various exemplary embodiments, the handle 110 comprises an elongate portion of material extending from a first end to a second end and having a longitudinal axis $L_H$. In certain exemplary embodiments, the handle 110 includes a knurled or textured portion 113, which allows the user to establish a more secure grip or purchase on the handle 110.

The static arm 120 extends from the handle 110 and includes a vial adapter recess or slot 122. The static arm 120 includes a longitudinal axis $L_{SA}$, and extends from the handle 110. In various exemplary embodiments, the static arm 120 extends from the handle 110 such that the longitudinal axis $L_{SA}$ of the static arm 120 is optionally substantially parallel to the longitudinal axis $L_H$ of the handle 110.

The vial adapter slot 122 is shaped so as to allow an IV bag vial adapter 182 to be secured within at least a portion of the vial adapter slot 122. The vial adapter slot 122 is generally keyway shaped so that a portion of the vial adapter 182 can be slid into the static arm 120, via the vial adapter slot 122, and then maintained in a relatively secure position relative to the vial adapter slot 122, until the vial adapter 182 is intentionally removed from the vial adapter slot 122.

In various exemplary embodiments, the vial adapter slot 122 comprises a recessed portion 123.

When the vial adapter 182 is secured within the vial adapter slot 122, a longitudinal axis $L_{AS}$ of the IV adapter spike 184 is maintained in a position substantially perpendicular to the longitudinal axis $L_{SA}$ of the static arm 120.

In certain exemplary embodiments, the static arm 120 is formed as an integral extension of the handle 110. Alternatively, the static arm 120 may be formed as a separate component that is attached or coupled to the handle 110. While the static arm 120 is generally attached or coupled to the handle 110 proximate the second end of the handle 110, it should be understood that the static arm 120 may extend from any portion of the handle 110.

The guide rod 130 comprises an elongate portion of material extending from a first end to a second end and having a longitudinal axis $L_{GR}$. The guide rod 130 extends from the static arm 120. In various exemplary, nonlimiting embodiments, the guide rod 130 extends from the static arm 120 such that the longitudinal axis $L_{GR}$ of the guide rod 130 is optionally substantially perpendicular to the longitudinal axis $L_{SA}$ of the static arm 120.

The guide rod 130 may be permanently or removably attached or coupled to the static arm 120.

In various exemplary embodiments, the guide rod 130 includes one or more stops 132 positioned proximate the first end or the second end of the guide rod 130. The stops 132, if included, serve to limit travel of the dynamic arm 140 relative to the guide rod 130. Typically, the stops 132 provide abutment surfaces to limit the travel of the dynamic arm 140 relative to the guide rod 130.

It should also be appreciated that, for simplicity and clarification, the various exemplary, nonlimiting embodiments of the vial attachment pliers 100 are shown and/or described with reference to the guide rod 130 and the corresponding aperture 146 having a relatively circular profile. However, the generally circular profile of the various guide rod 130 and aperture 146 are intended to be illustrative, not limiting the profile or geometry of the guide rod 130 and aperture 146 to any particular shape. It should be understood that the overall profile and/or geometry of the guide rod 130 and corresponding aperture 146 may comprise any overall profile or geometry, including, for example, a generally square, rectangle, triangular, pentangular, circular, oval, elliptical, elliptical torus, star, or other shape.

Thus, it should be appreciated that the profile or geometry of the guide rod 130 and corresponding aperture 146 of the vial attachment pliers 100 of this invention is a design choice based on the desired appearance, strength, and functionality of the vial attachment pliers 100.

The dynamic arm 140 comprises a portion of material having a longitudinal axis $L_{DA}$ and including a vial recess or slot 142. The dynamic arm 140 is slidably attached to the guide rod 130, via an aperture 146, such that the dynamic arm 140 is slidable along at least a portion of the guide rod 130. Through the interaction of the aperture 146 and the guide rod 130, the longitudinal axis $L_{DA}$ of the dynamic arm 140 remains substantially parallel to the longitudinal axis $L_{SA}$ of the static arm 120 at all points as the dynamic arm 140 slides along the guide rod 130. Thus, as the dynamic arm 140 slides along the guide rod 130, the longitudinal axis $L_{DA}$ of the dynamic arm 140 is always maintained in a position substantially parallel to the longitudinal axis $L_{SA}$ of the static arm 120.

The dynamic arm 140 includes a vial slot 142 that is shaped so as to allow a neck of the vial 190 to be secured within at least a portion of the vial slot 142. The vial slot 142 is generally "U" or keyway shaped so that at least the neck portion of the vial 190 can be slid into the dynamic arm 140, via the vial slot 142, and then maintained in a relatively secure position relative to the vial slot 142, until the vial 190 is intentionally removed from the vial slot 142.

When the vial 190 is secured within the vial slot 142, the IV adapter spike 184 is maintained in a position substantially perpendicular to the longitudinal axis $L_{SA}$ of the dynamic arm 140.

In various exemplary embodiments, the vial slot 142 includes at least some cushioning material 144. The cushioning material 144, if included, allows the vial 190 to be frictionally maintained within the vial slot 142 and/or provides a certain amount of cushioning to the vial slot 142 so as to reduce the possibility of the vial 190 being damaged or broken when maintained within the vial slot 142.

The lever 150 comprises an elongate portion of material extending from a first end to a second end. In certain exemplary embodiments, the lever 150 includes a knurled or textured portion 153, which allows the user to establish a more secure grip or purchase on the lever 150.

The lever 150 also includes an elongate aperture 152 that allows at least a portion of the handle 110 to be positioned within and through the aperture 152 of the lever 150.

The lever 150 is pivotably attached, via a pivot pin 170, to the handle 110. In this manner, the lever 150 is able to pivot relative to the handle 110 between an open position and a closed position.

In various exemplary embodiments, the handle 110 includes a protrusion or stop 112 and the lever 150 includes a protrusion or stop 152. The stops 112 and 152 are positioned such that when the lever 150 is pivoted to the closed position, engaging surfaces of the stops 112 and 150 to make contact and limit further travel of the lever 150 relative to the handle 110.

Figure 4:
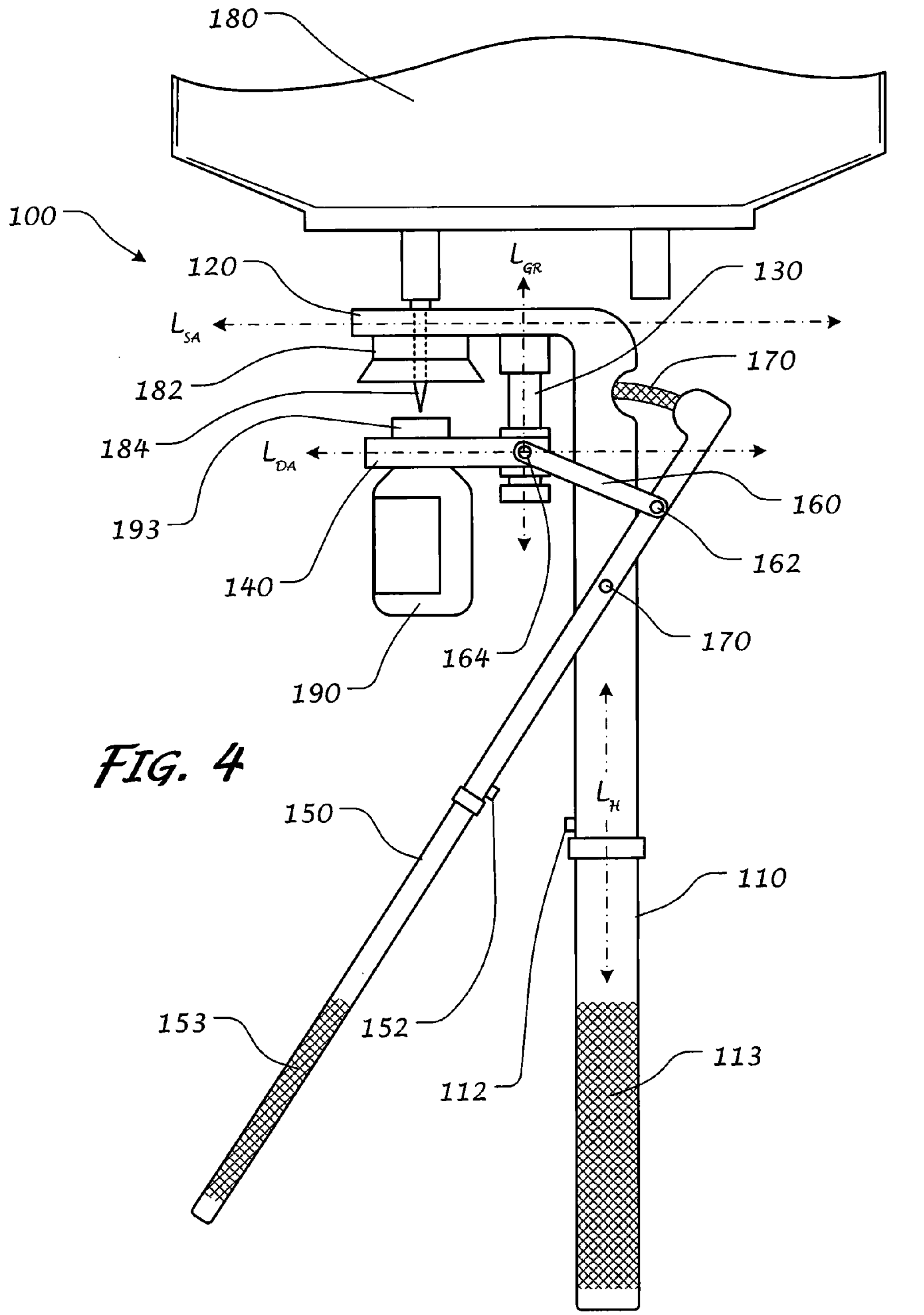
FIG. 4 shows a side view of an exemplary embodiment of vial attachment pliers, wherein the lever is pivoted to an open position, according to this invention.
Figure 5:
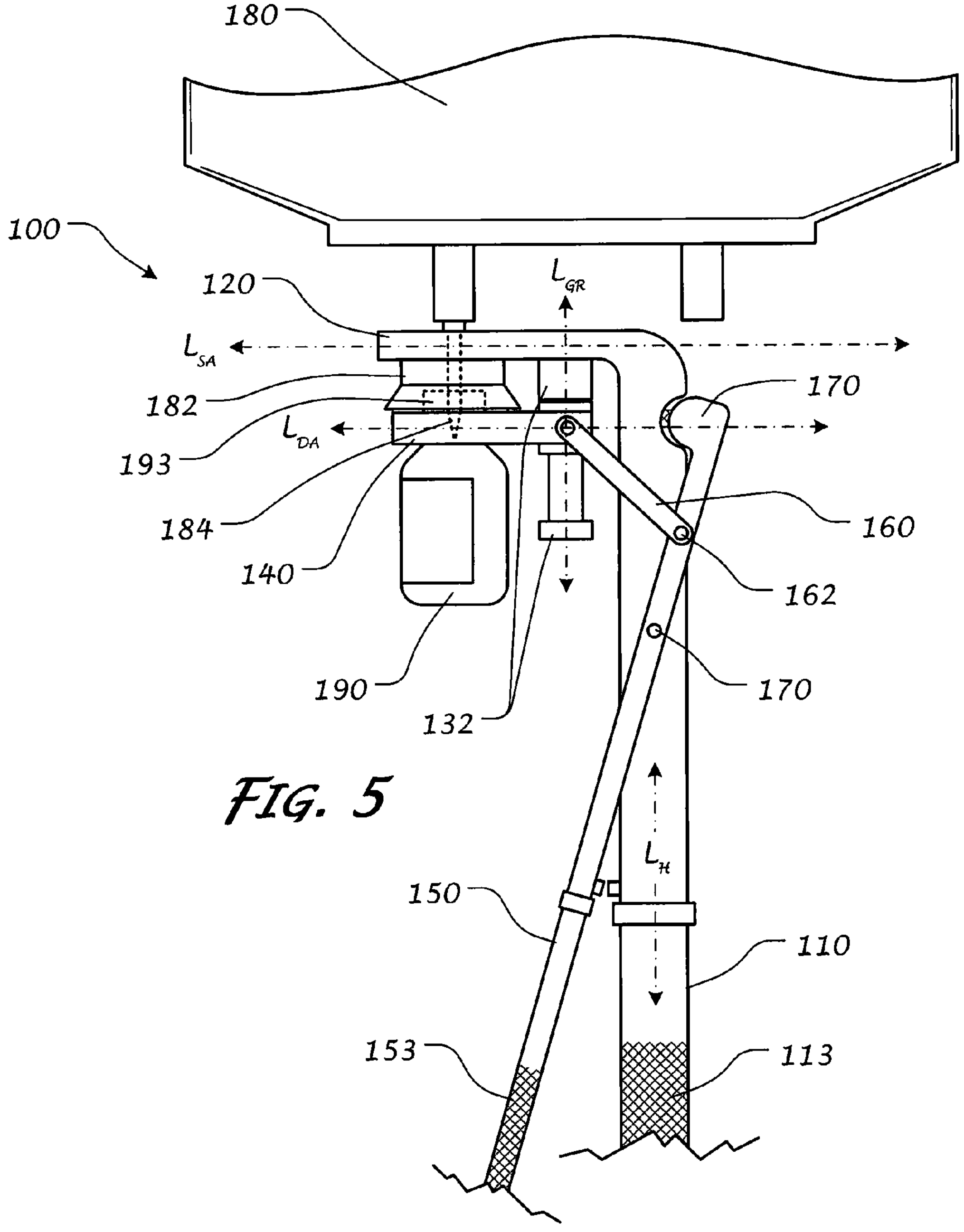
FIG. 5 shows a side view of an exemplary embodiment of vial attachment pliers, wherein the lever is pivoted to a closed position, according to this invention.
Figure 6:
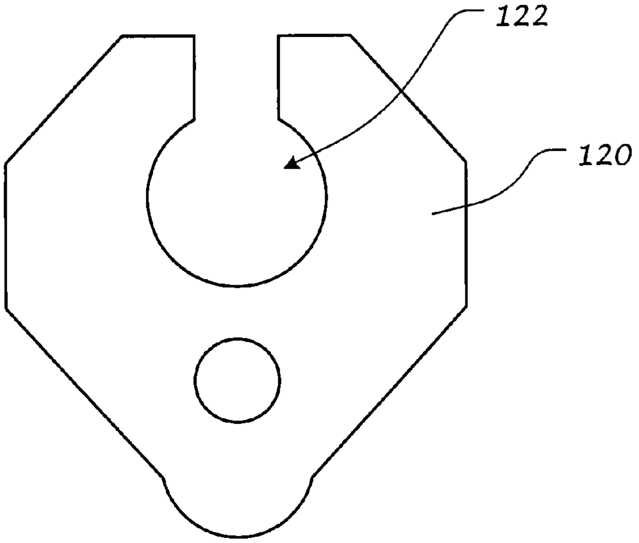
FIG. 6 shows a top view of an exemplary embodiment of a static arm of an exemplary embodiment of vial attachment pliers, according to this invention.
Figure 7:
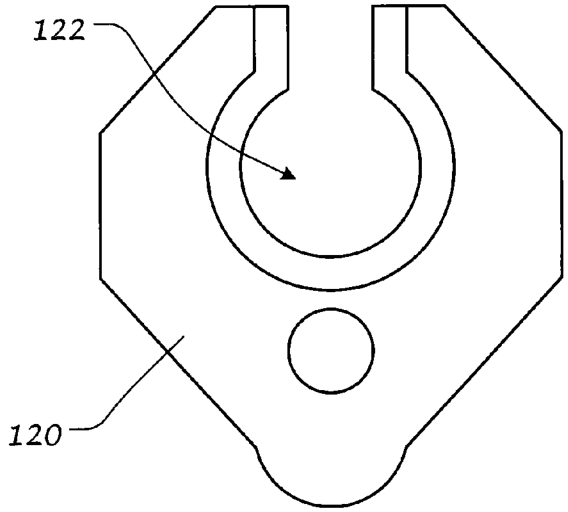
FIG. 7 shows a bottom view of an exemplary embodiment of a static arm of an exemplary embodiment of vial attachment pliers, according to this invention.

The connector bar 160 comprises an elongate portion of material that is pivotably attached or coupled, via a pivot pins 162 and 164, between the lever 150 and the dynamic arm 140, respectively. The connector bar 160 is substantially rigid and is connected between the lever 150 and the dynamic arm 140 such that as the lever 150 pivots relative to the handle 110, the dynamic arm 140 is urged to slide along the portion of the guide rod 130. Thus, as the lever 150 is pivoted to the open position, as illustrated in FIG. 4, the connector bar 160 urges the dynamic arm 140 to slide downward, along the guide rod 130 and increase the distance between the static arm 120 and the dynamic arm 140. Conversely, as the lever 150 is pivoted to the closed position, as illustrated in FIG. 5, the connector bar 160 urges the dynamic arm 140 to slide upward, along the guide rod 130 and decreased the distance between the static arm 120 and the dynamic arm 140.

In various exemplary, nonlimiting embodiments, a spring or other resilient material 170 is provided between a portion of the lever 150 and the handle 110, so as to provide a springing, rebounding, or dampening force to the pivoting movement of the lever 150 relative to the handle 110. Typically, but not exclusively, the resilient material 170 may optionally be provided between an area proximate the second end of the handle 110 and an area proximate the second end of the lever 150.

In various exemplary embodiments, various components of the vial attachment pliers 100 are substantially rigid and are formed of stainless steel. Alternate materials of construction of the various components of the vial attachment pliers 100 may include one or more of the following: wood, steel, aluminum, titanium, and/or other metals, as well as various alloys and composites thereof, glass-hardened polymers, polymeric composites, polymer or fiber reinforced metals, carbon fiber or glass fiber composites, continuous fibers in combination with thermoset and thermoplastic resins, chopped glass or carbon fibers used for injection molding compounds, laminate glass or carbon fiber, epoxy laminates, woven glass fiber laminates, impregnate fibers, polyester resins, epoxy resins, phenolic resins, polyimide resins, cyanate resins, high-strength plastics, nylon, glass, or polymer fiber reinforced plastics, thermoform and/or thermoset materials, and/or various combinations of the foregoing. Thus, it should be understood that the material or materials used to form the various components of the vial attachment pliers 100 is a design choice based on the desired appearance and functionality of the vial attachment pliers 100.

It should be appreciated that certain elements of the vial attachment pliers 100 may be formed as an integral unit (such as, for example, the handle 110 and the static arm 120). Alternatively, suitable materials can be used and sections or elements made independently and attached or coupled together, such as by adhesives, welding, screws, rivets, pins, or other fasteners, to form the various elements of the vial attachment pliers 100.

It should also be understood that the overall size and shape of the vial attachment pliers 100, and the various portions thereof, is a design choice based upon the desired functionality and/or appearance of the vial attachment pliers 100.

To use the vial attachment pliers 100 to connect a vial 190 to an IV bag 180, the lever 150 is pivoted to an open position relative to the handle 110 and an appropriate portion of an IV vial adapter 182 of an IV bag 180 is positioned within the vial adapter slot 122 of the static arm 120. Then, the neck portion of an appropriate vial 190 is positioned within the vial slot 142 of the dynamic arm 140. When the vial 190 is correctly positioned within the vial slot 142, the vial stopper 193 should be roughly centered below the IV adapter spike 184.

Once the IV vial adapter 182 and the vial 190 are correctly secured to the vial attachment pliers 100, the lever 150 is pivoted toward the closed position relative to the handle 110 and the connector bar 160 urges the dynamic arm 140 (and the vial 190) toward the static arm 120 (and the IV vial adapter 182 and IV adapter spike 184).

As the lever 150 continues to be pivoted towards the closed position, the IV adapter spike 184 first engages and then punctures the vial stopper 193. As the lever 150 reaches the closed position, the IV adapter spike 184 is forced through the vial stopper 193 so as to establish a fluid connection between the interior of the vial 190 and the interior of the IV bag 180. If desired, the vial attachment pliers 100 may then be removed from the connected vial 190 and IV bag 180 by withdrawing the IV vial adapter 182 and the vial 190 from the vial adapter slot 122 and the vial slot 142, respectively.

To use the vial attachment pliers 100 to remove a connected vial 190 from an IV bag 180, and appropriate portion of the IV vial adapter 182 is positioned within the vial adapter slot 122 while the neck portion of the vial 190 is simultaneously positioned within the vial slot 142. Once appropriately positioned, the lever 150 is merely pivoted to the open position to remove the connected vial 190 from the IV vial adapter 182 of the IV bag 180.

While this invention has been described in conjunction with the exemplary embodiments outlined above, the foregoing description of exemplary embodiments of the invention, as set forth above, are intended to be illustrative, not limiting and the fundamental invention should not be considered to be necessarily so constrained. It is evident that the invention is not limited to the particular variation set forth and many alternatives, adaptations modifications, and/or variations will be apparent to those skilled in the art.

Furthermore, where a range of values is provided, it is understood that every intervening value, between the upper and lower limit of that range and any other stated or intervening value in that stated range is encompassed within the invention. The upper and lower limits of these smaller ranges may independently be included in the smaller ranges and is also encompassed within the invention, subject to any specifically excluded limit in the stated range. Where the stated range includes one or both of the limits, ranges excluding either or both of those included limits are also included in the invention.

It is to be understood that the phraseology of terminology employed herein is for the purpose of description and not of limitation. Unless defined otherwise, all technical and scientific terms used herein have the same meaning as commonly understood by one of ordinary skill in the art to which this invention belongs.

In addition, it is contemplated that any optional feature of the inventive variations described herein may be set forth and claimed independently, or in combination with any one or more of the features described herein.

Accordingly, the foregoing description of exemplary embodiments will reveal the general nature of the invention, such that others may, by applying current knowledge, change, vary, modify, and/or adapt these exemplary embodiments for various applications without departing from the spirit and scope of the invention. Any and all such changes, variations, modifications, and/or adaptations should and are intended to be comprehended within the meaning and range of equivalents of the disclosed exemplary embodiments and may be substituted without departing from the true spirit and scope of the invention.

What is claimed is:

1. Vial attachment pliers, comprising:

an elongate handle having a longitudinal axis;

a static arm having a longitudinal axis, wherein the static arm extends from the handle such that the longitudinal axis of the static arm is substantially perpendicular to the longitudinal axis of the handle, and wherein the static arm includes a vial adapter slot;

a guide rod having a longitudinal axis, wherein the guide rod extends from the static arm such that the longitudinal axis of the guide rod is substantially perpendicular to the longitudinal axis of the static arm;

a dynamic arm having a longitudinal axis, wherein the dynamic arm is slidably attached to the guide rod such that the dynamic arm is slidable along at least a portion of the guide rod, wherein the longitudinal axis of the dynamic arm remains parallel to the longitudinal axis of the static arm as the dynamic arm slides along the guide rod, and wherein the dynamic arm includes a vial slot;

a lever, wherein the lever is pivotably attached to the handle;

a connector bar connecting the lever to the dynamic arm, such that as the lever pivots relative to the handle, the dynamic arm is urged to slide along the portion of the guide rod.

2. The vial attachment pliers of claim 1, wherein the elongate handle includes a stop for limiting travel of the lever relative to the handle.

3. The vial attachment pliers of claim 1, wherein the elongate handle includes a knurled portion.

4. The vial attachment pliers of claim 1, wherein the lever includes a stop for limiting travel of the lever relative to the handle.

5. The vial attachment pliers of claim 1, wherein the lever includes a knurled portion.

6. The vial attachment pliers of claim 1, wherein the vial adapter slot is adapted to receive at least a portion of an IV bag vial adapter.

7. The vial attachment pliers of claim 1, wherein the vial adapter slot is keyway shaped.

8. The vial attachment pliers of claim 1, wherein the vial slot is adapted to receive at least a portion of a vial.

9. The vial attachment pliers of claim 1, wherein the vial slot includes at least some cushioning material.

10. The vial attachment pliers of claim 1, wherein the guide rod includes one or more stops for limiting travel of the dynamic arm relative to the guide rod.

11. The vial attachment pliers of claim 1, wherein lever includes an elongate aperture that allows at least a portion of the handle to be positioned within and through the aperture of the lever.

12. Vial attachment pliers, comprising:

a handle having a longitudinal axis;

a static arm having a longitudinal axis, wherein the static arm extends from the handle, and wherein the static arm includes a vial adapter slot;

a guide rod having a longitudinal axis, wherein the guide rod extends from the static arm;

a dynamic arm having a longitudinal axis, wherein the dynamic arm is slidably attached to the guide rod such that the longitudinal axis of the dynamic arm is substantially parallel to the longitudinal axis of the static arm, and wherein the dynamic arm includes a vial slot;

a lever, wherein the lever is pivotably attached to the handle; and a connector bar connecting the lever to the dynamic arm, such that as the lever pivots relative to the handle, the dynamic arm is urged to slide along a portion of the guide rod.

13. The vial attachment pliers of claim 12, wherein the vial adapter slot is adapted to receive at least a portion of an IV bag vial adapter.

14. The vial attachment pliers of claim 12, wherein the vial adapter slot is keyway shaped.

15. The vial attachment pliers of claim 12, wherein the vial slot is adapted to receive at least a portion of a vial.

16. The vial attachment pliers of claim 12, wherein the vial slot includes at least some cushioning material.

17. The vial attachment pliers of claim 12, wherein the guide rod includes one or more stops for limiting travel of the dynamic arm relative to the guide rod.

18. The vial attachment pliers of claim 12, wherein lever includes an elongate aperture that allows at least a portion of the handle to be positioned within and through the aperture of the lever.

19. Vial attachment pliers, comprising:

a handle;

a static arm that extends from the handle, wherein the static arm includes a vial adapter slot;

a guide rod extending from the static arm;

a dynamic arm slidably attached to the guide rod, wherein the dynamic arm includes a vial slot;

a lever, wherein the lever is pivotably attached to the handle; and a connector bar connecting the lever to the dynamic arm, such that as the lever pivots relative to the handle, the dynamic arm is urged to slide along a portion of the guide rod, and wherein as the dynamic arm is urged to slide along a portion of the guide rod, a longitudinal axis of the dynamic arm is substantially parallel to a longitudinal axis of the static arm.

* * * * *